(12) United States Patent  (10) Patent No.: US 8,157,775 B2
Bobroff et al.  (45) Date of Patent: Apr. 17, 2012

(54) POSTOPERATIVE FLUID MONITORING AND ALERT SYSTEM

(75) Inventors: Alec Bobroff, Norfolk, MA (US); Clifford Ross Martin, Medway, MA (US); Phillip B. Dolliver, Framingham, MA (US)

(73) Assignee: Haemonetics Corporation, Braintree, MA (US)

( * ) Notice: Subject to any disclaimer, the term of this patent is extended or adjusted under 35 U.S.C. 154(b) by 942 days.

(21) Appl. No.: 10/798,060

(22) Filed: Mar. 10, 2004

(65) Prior Publication Data

US 2005/0203469 A1   Sep. 15, 2005

(51) Int. Cl.
*A61M 1/00* (2006.01)
(52) U.S. Cl. .................................. 604/319; 604/313
(58) Field of Classification Search .................. 604/313, 604/319
See application file for complete search history.

(56) References Cited

U.S. PATENT DOCUMENTS

| 4,343,316 | A | * | 8/1982 | Jespersen | 600/584 |
| 4,464,172 | A | * | 8/1984 | Lichtenstein | 604/65 |
| 4,658,834 | A | * | 4/1987 | Blankenship et al. | 600/584 |
| 4,735,610 | A | * | 4/1988 | Akkas et al. | 604/119 |
| 5,153,828 | A | * | 10/1992 | Inoue et al. | 600/573 |
| 5,665,061 | A | * | 9/1997 | Antwiler | 604/6.07 |
| 5,876,387 | A | * | 3/1999 | Killian et al. | 604/319 |
| 5,891,051 | A | * | 4/1999 | Han et al. | 600/573 |
| 5,989,234 | A | * | 11/1999 | Valerio et al. | 604/321 |
| 6,346,096 | B1 | * | 2/2002 | Yam et al. | 604/321 |
| 6,749,592 | B2 | * | 6/2004 | Lord | 604/319 |
| 2002/0030322 | A1 | * | 3/2002 | Connelly | 273/243 |
| 2002/0193761 | A1 | * | 12/2002 | Lord | 604/323 |

* cited by examiner

*Primary Examiner* — Melanie Hand
(74) *Attorney, Agent, or Firm* — John F. Perullo

(57) ABSTRACT

Continuous performance monitoring and an automated alert system are provided for a postoperative fluid drainage procedure. The system uses an automated controller in communication with at least one sensor that monitors the amount of liquid collected during the procedure. The controller compares current collection data with historical collection data to identify trends that can be indicative of problems in the patient's recovery or in system drainage. Upon identifying such trends, the controller automatically provides an alarm to alert the care provider so that the system can be checked and remedial action taken.

14 Claims, 8 Drawing Sheets

POSTOPERATIVE FLUID MONITORING AND ALERT SYSTEM

FIELD OF THE INVENTION

This invention pertains to devices and methods for postoperative collection of blood and other fluids from a surgical site. In particular, the invention relates to a system for monitoring such procedures and providing means for alerting a care provider of changes in drainage status.

BACKGROUND OF THE INVENTION

Postoperative drainage of blood and other fluids that tend to collect at a surgical site is necessary to promote proper healing and prevent harm to surrounding tissues and organs. Drainage at the surgical site is particularly important in procedures carried out in the chest cavity, such as cardiac or spine procedures. Without proper drainage, the pooling of blood and fluid in the chest cavity can prevent the lungs from fully expanding to allow normal breathing, which could endanger a patient's life.

Commonly used devices for managing the collection of blood and fluid from a surgical site in a postoperative environment are disposable, relatively simple and lack automated controls. Examples of commonly used devices include the Pleura Vac S-1100 made by Genzyme Corporation of Fall River, Mass. and the Atrium Oasis # AW002714-003B available from Atrium Medical Corporation of Hudson, N.H. Such devices comprise a light weight portable container having a serpentine fluid pathway into which blood and fluid from the patient is aspirated. The devices rely on an external source of vacuum to aspirate the fluid, such as connection to a wall suction port accessing a facility wide vacuum system, which is available in many hospitals. At the end of the serpentine fluid pathway is provided a column of water, sealing the patient side of the pathway from the vacuum source side of the pathway. The column of water serves as a seal to prevent reversal of flow back to the patient if suction is discontinued.

The process of postoperative surgical site drainage can also provide an indication to the health care provider of the status of surgical wound condition. Normal healing of the surgical wound is indicated by a steady decrease over time in the amount of blood and fluid collected from the surgical site. An unexpected cessation of fluid collection may be an indication of a blockage in the drain tube created by blood clotting. Such a blockage requires attention by the care provider to reestablish drainage flow. Continuing high amounts of fluid collection or a sudden increase in fluid collection after a period of reduced amounts of collected fluid may indicate bleeding at the surgical site that requires attention of the care provider.

Because the known manual collection devices mentioned above lack automated controls, the progress of fluid collection must be monitored actively by the care provider. To observe the indications of wound status mentioned above, the care provider must return to the collection device at regular time intervals and visually observe the amount of fluid that has been collected since the last observation. Such labor-intensive monitoring is wasteful of the care provider's time and endangers the patient because problems that arise between observation visits will not be noticed until the next regularly scheduled status check is made by the care provider.

It would be desirable to provide a postoperative fluid drain system that continuously monitors the drainage process and automatically alerts care providers when drainage flow characteristics indicate a potential problem with the process. It is an object of the present invention to provide such a system.

SUMMARY OF THE INVENTION

The present invention provides a system for the continuous performance monitoring of a surgical wound drainage procedure. The monitoring system is also configured to activate an alarm to alert care providers when certain performance trends are identified that are indicative of problem with the procedure. The system includes a fluid collection device having access to a vacuum reservoir. The collection device is configured to be joined to a surgical drain tube and a drainage catheter at the surgical site of the patient. A suction pathway is created through the catheter, drain tube and collection device to aspirate blood another fluids away from the surgical site. Collected fluid is drawn to a collection vessel external to the patient for disposal or later processing. The fluid collection device may be configured as an autotransfusion device that operates to collect blood and fluid drained from the surgical site, cleans it and returns the blood to the patient. Though the system is most useful in monitoring postoperative fluid collection procedures, it may be integrated with peri-operative fluid collection systems and configured to run in an intra-operative mode or postoperative mode.

The vacuum reservoir may be part of the fluid collection device system and may comprise a vacuum tank in fluid communication with the suction pathway defined by the drain tube and drainage catheter. The vacuum reservoir may be connected to an on-board suction pump to replenish suction as needed. Alternatively, the vacuum reservoir may be configured as a vacuum tank that is configured to be removed when it becomes depleted and is replaced with a tank having a refreshed vacuum reservoir. Another alternative is to join the suction pathway to a wall-suction port accessing a facility-wide source of vacuum.

The system includes an automated controller preferably operated by a computer readable medium and that is connected to one or more sensors configured to observe fluid drainage performance along the suction pathway. Information regarding fluid drainage procedure performance is returned to the controller by the one or more sensors. The controller provides access to the current performance data to a care provider in a convenient form. The controller also keeps track of past performance data from the procedure, historical data, and continuously compares current data with historical data to identify performance trends that are indicative of conditions that may be relevant to the patient's recovery process. The controller is configured to activate an alarm to alert a care provider if a potentially harmful performance trend is identified.

To sense conditions in the fluid/suction pathway of the system, one or more sensors connected to the controller are employed. One sensor should be configured to sense and transmit back to the controller how much liquid has been collected through the suction pathway. A sensor configuration to accomplish that task incorporates an optical viewing means, such as a camera, to observe the liquid level in the fluid collection vessel. Another sensor that may be included to monitor process performance is a pressure sensor configured to detect suction level in the suction pathway. As the controller monitors suction levels in the pathway, it may also be connected to an electronically controllable valve that is configured to selectively open the suction pathway to the vacuum reservoir upon signal from the controller. The frequency of valve openings may also be monitored by the controller. If an on-board compressor is included, the controller may be connected to it and configured to operate the compressor when information from a pressure sensor indicates that the vacuum reservoir is depleted.

In the case of fluid collection device that is an autotransfusion device the controller may be configured to control operation of the autotransfusion process. In particular, when the controller receives information that a sufficient amount of liquid has been collected in the collection vessel, the controller can signal the autotransfusion device to initiate processing of the liquid. While liquid is directed from the collection vessel to the autotransfusion device, the controller records how much liquid was removed for processing and keeps track of the total amount of liquid that has been removed from the patient. Other system parameters that may be monitored by the controller include process status (on, off or standby), suction status in the pathway (on or off), process run time, total liquid volume collected.

The controller is also preferably connected to a visual display such as a video monitor screen to communicate information to the care provider. The controller may display fluid collection information visually by presenting a numerical data and process status information. The display may be configured to provide information graphically, such as in a bar graph.

In operation, during a surgical wound drainage procedure, the system monitors fluid collected from the patient and the controller saves the collection information in a historical record. The historical data information is used by the controller for several purposes. First, the controller uses the historical data to create a record that may be presented on the visual display so that the care provider can quickly determine the progress of patient recovery and surgical wound healing based on the amount of liquid collected from the surgical site over time. For example, a graphical representation of how much liquid has been collected over a period of several finite time intervals may be displayed graphically on the visual display, such as in a bar graph.

One example of a graphical representation of fluid collection is a bar graph showing the volume of fluid collected, represented along the Y-axis, over a period of time, measured along the X-axis. Finite time intervals may be selected that are comparable to the intervals between manual checks of prior art drain devices by care provider staff. For example, fifteen minute intervals may be displayed on the graph such that the single vertical bar rising from the X-axis shows a volume of liquid collected in total during a 15 minute period of time. A plurality of such bars showing quantities collected in previous time intervals may be shown for historical reference. In addition, current flow information is shown graphically as the last bar in the series. Because the latest bar represents a time period that is ongoing, the total quantity of liquid will be changing instantaneously until the time interval is completed, at which point the graphical representation of quantity will freeze to represent the total quantity collected during that time interval. The bar will then become part of the historical flow data and a new variable bar will appear to represent the current flow data. Visual cues may be employed to help the care provider distinguish between historical information and the current information, such as different colors used for the historical and current collection bars.

Historical and current collection information is maintained by the controller not only for observation and review by the care provider, but also for detection by the controller of meaningful trends that are indicative of patient status and system performance. The controller is programmed to compare current collection data with historical collection data over one or more time intervals and to identify trends in the data relevant to collection performance. If one of several predefined trends indicative of a problem in the process or patient condition is detected, the controller can be configured to activate an alarm to notify the care provider so that investigation and possible remedial action can be undertaken. For example, a trend that shows a sudden cessation of flow may indicate that the surgical drain tube has become plugged, such as by clotting of blood. A trend that shows continuous high levels of fluid collection or a sudden increase of level of fluid collection after several periods of decreasing fluid collection may indicate a bleeding problem at the surgical site.

In addition to monitoring liquid collection and identifying trends in amounts collected, the controller may be configured to monitor suction in the suction pathway and identify trends that indicate vacuum leaks in the system. Specifically, the controller is connected to a valve in the suction pathway that is selectively opened to the vacuum reservoir to replenish suction to the suction pathway as needed. The controller monitors how frequently the valve must be opened over time in order to maintain adequate suction levels in the pathway. If the valve must be opened repeatedly to maintain suction in the pathway that preferably mimics a closed system, a trend can be identified that suggests that there is a leak somewhere along the pathway that is permitting reduction of the pathway suction level. Such leaks can occur at the point where the drain catheter enters the patient's body. Because the presence of a vacuum leak reduces the effectiveness of the fluid draining, the controller may be configured to notify the care provider with an alarm if the number of vacuum valve cycles exceeds a predetermined value over a period of time.

Notification to the care provider of the identification of such trends in the drainage procedure may be made by an audible or visual alarm initiated by the controller. An audible alarm should be sufficiently loud to notify a care provider that is not necessarily immediately adjacent to the system. A visual alarm may be presented on the visual display and provide information about the type of condition detected. Either one or both of the visual and audible alarms may be provided with the system. Another mechanism for alerting care providers to an alarm condition may comprise sending notification directly to a central nursing station. In this scenario, the controller is provided with appropriate network interface hardware to connect with the facility information system such as by using Ethernet hardware for example.

It is an object of the present invention to provide a post operative fluid monitoring and alert system that tracks the amount of liquid being collected, retains historical fluid information, compares current liquid collection information with the historical liquid collection information and identifies trends that are relevant to the procedure performance or to the patient's condition.

It is another object of the invention to provide a post operative fluid monitoring and alert system that is compatible for use with post operative fluid collection devices and autotransfusion systems, especially such systems compatible for use in surgical procedures carried out in the chest cavity.

It is another object of the invention to provide a method of monitoring a post operative fluid drainage procedure that provides a liquid collection sensor connected to a controller that is configured to receive current liquid collection information and retain historical liquid collection information and present that information in a convenient form to a care provider.

It is another object of the invention to provide a method of monitoring a postoperative fluid collection procedure comprising providing a controller configured to compare current liquid collection information with historical liquid collection information, identify collection trends and activate an alarm if a trend that is potentially harmful to the patient is detected.

BRIEF DESCRIPTION OF THE DRAWINGS

The foregoing and other objects and advantages will be appreciated more fully from the following further description thereof, with reference to the accompanying diagrammatic drawings wherein.

DESCRIPTION OF THE ILLUSTRATIVE EMBODIMENTS

Figure 1:
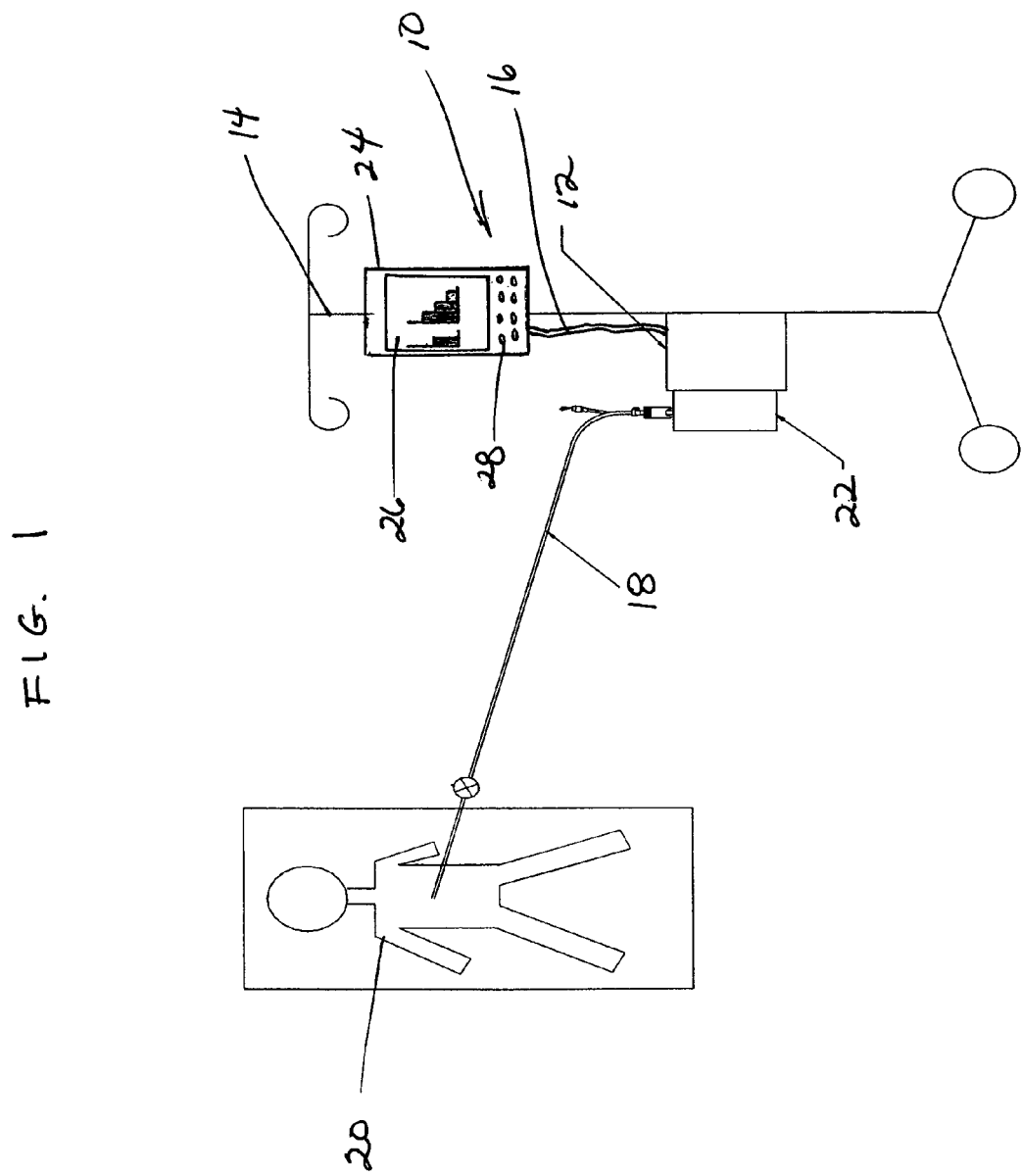
FIG. 1 is a diagrammatic illustration of the fluid monitoring and alert system in combination with a fluid collection device joined to a surgical drain tube leading to a patient.

FIG. 1 shows a diagrammatical illustration of a postoperative fluid monitoring and alert system 10 in combination with a fluid collection device 12. The monitoring and alert system 10 may be mounted together with the collection device 12, such as on an I.V. pole 14, and connected together by a communication conduit 16 such as wiring. The fluid collection device 12 is joined to a surgical wound drain tube 18 that leads to a drain catheter (not shown) positioned internally at the surgical site of a patient 20.

During a surgical drainage procedure, suction is applied to a fluid collection vessel 22 of the fluid collection device 12 and to drain tube 18 to aspirate blood and other fluids through the drain catheter placed at the surgical site. Interior passages of the drain catheter, drain tube, collection vessel and collection device define a suction pathway through which fluid can be aspirated from the surgical site. Fluids collected at postoperative surgical site include liquids such as blood and lavage substances introduced during the surgical procedure as well as air that enters during the procedure and becomes trapped after closure of the wound. Drainage of the liquids such as blood from a postoperative surgical site is important to promote healing of tissues at the site. Without drainage, the accumulation of liquids at the surgical site could interfere with the function of vital organs such as the lungs or heart, such as in the case of surgical procedure carried out in the chest cavity.

It is noted that suction applied to the surgical site also serves to remove trapped air, which is desirable to reduce patient discomfort and to help organs return to their original pre-procedure state and position. However in monitoring the progress of patient recovery and wound healing, it is more important (and reliable) to focus attention on the amount of liquid recovered from the surgical site. The system of the present invention monitors a surgical wound fluid drainage procedure by observing the amount of liquid collected during the process. A properly operating fluid drainage process as determined by monitoring the liquid collected will inevitably serve to drain all undesirable fluids from the surgical site including gas such as air.

Fluid aspirated through drain tube 18 collects in vessel 22 and later may be disposed of or cleaned and the blood returned to the patient in the case of a fluid collection device 12 configured as an autotransfusion device. The fluid monitoring and alert system 10 senses and keeps track of the amount of liquid collected in vessel 22 over time. The system identifies trends in the fluid collection procedure that indicate conditions that may be harmful to the patient and alerts the care provider of such trends.

The monitoring and alert system 10 comprises a controller 24 configured to be programmed with a computer readable medium. The controller is contained within a housing that may be securable adjacent to a connected fluid collection device such as being mountable on an I.V. pole that is shared with the collection device. The housing may also include a visual display 26 and user input controls 28 that are connected to the controller. The controller is connected to one or more sensors and fluid controls mounted in the fluid collection device. The communication conduit 16 may comprise a bundle of wires each of which establishes a direct connection between a sensor and a receptacle on the controller. An example of controller suitable for use in the present invention is the Phillips 1L 80C32 controller.

Figure 2:
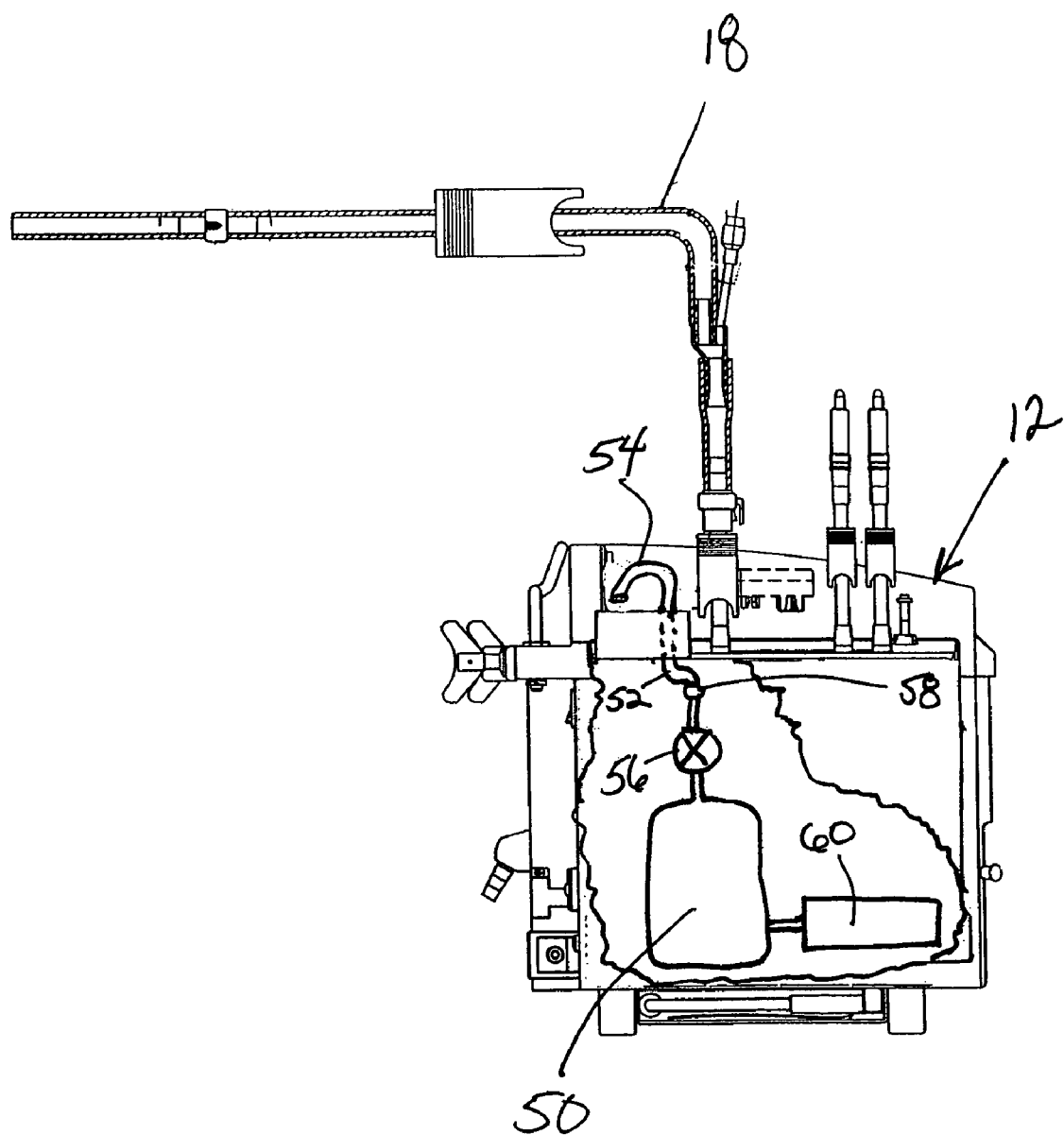
FIG. 2 is a partial cut-away view of fluid collection device showing internal vacuum reservoir components.

FIG. 2 shows a partial cutaway view of the fluid collection device 12 that may be employed in combination with the monitoring and alert system 10 discussed above. Housed within the collection device are components that provide a source of suction to aspirate fluid from the surgical site. The source of suction may be a vacuum reservoir 50 housed within the fluid collection device 12. The vacuum reservoir 50 may be a tank configured to hold negative pressure that may be opened to fluid communication with the fluid collection vessel 22 via inner conduit 52 and vessel conduit 54, which leads from the opening of inner conduit 52 to the top of the fluid collection vessel 22. Introduction of vacuum to the vessel 22 serves to aspirate fluid from the surgical site through the drain tube 18.

Communication between the vacuum reservoir 50 and the inner conduit 52 is selectively controlled via a suction valve 56. The suction valve 56 may be an electro-mechanically controlled unit that is operated under command of the system controller. An example of a valve suitable for this application is the Pneutronics Series II PC Mount Digital Solenoid Valve.

A pressure sensor 58 is in fluid communication with the suction pathway defined by conduits 52 and 54, vessel 22 and drain tube 18. The pressure sensor 58 is configured to sense the negative pressure experienced in the suction pathway and provides continuous information to the system controller 24 regarding the magnitude of the suction levels in the pathway. An example of a pressure sensor suitable for this application is the Motorola MPX Series 5000 sensor. A redundant set-up of two pressure sensors may be employed, with the controller monitoring readings from both sensors to ensure that a malfunctioning sensor is detected if readings do not match. When the suction level monitored by the pressure sensor 58 reduces in magnitude, as routinely happens as liquid periodically drips from the drain 18 to the vessel 22, the controller signals the valve 56 to open to the vacuum reservoir 50 until an appropriate suction level is achieved in the suction pathway. When the pressure sensor indicates an adequate suction level has again been achieved, the controller closes the valve 56.

After repeated opening of the valve 56, the suction level in the reservoir 50 may become depleted and require further reduction in pressure (increase in vacuum). To reestablish adequate vacuum in the reservoir, the collection device 12 may be provided with an on-board compressor 60, in fluid communication with the vacuum reservoir. The compressor may be periodically activated by the system controller to increase the vacuum level in the vacuum reservoir 50 when needed as based on information obtained from pressure sensor 58. Alternatively, it should be appreciated by those skilled in the art that the vacuum tank and compressor system described above may be replaced by an external vacuum tank that is exchangeable or by connection to a facility wide source of vacuum via a wall suction port. Such variations are not considered to depart from the scope of the invention.

Figure 3:
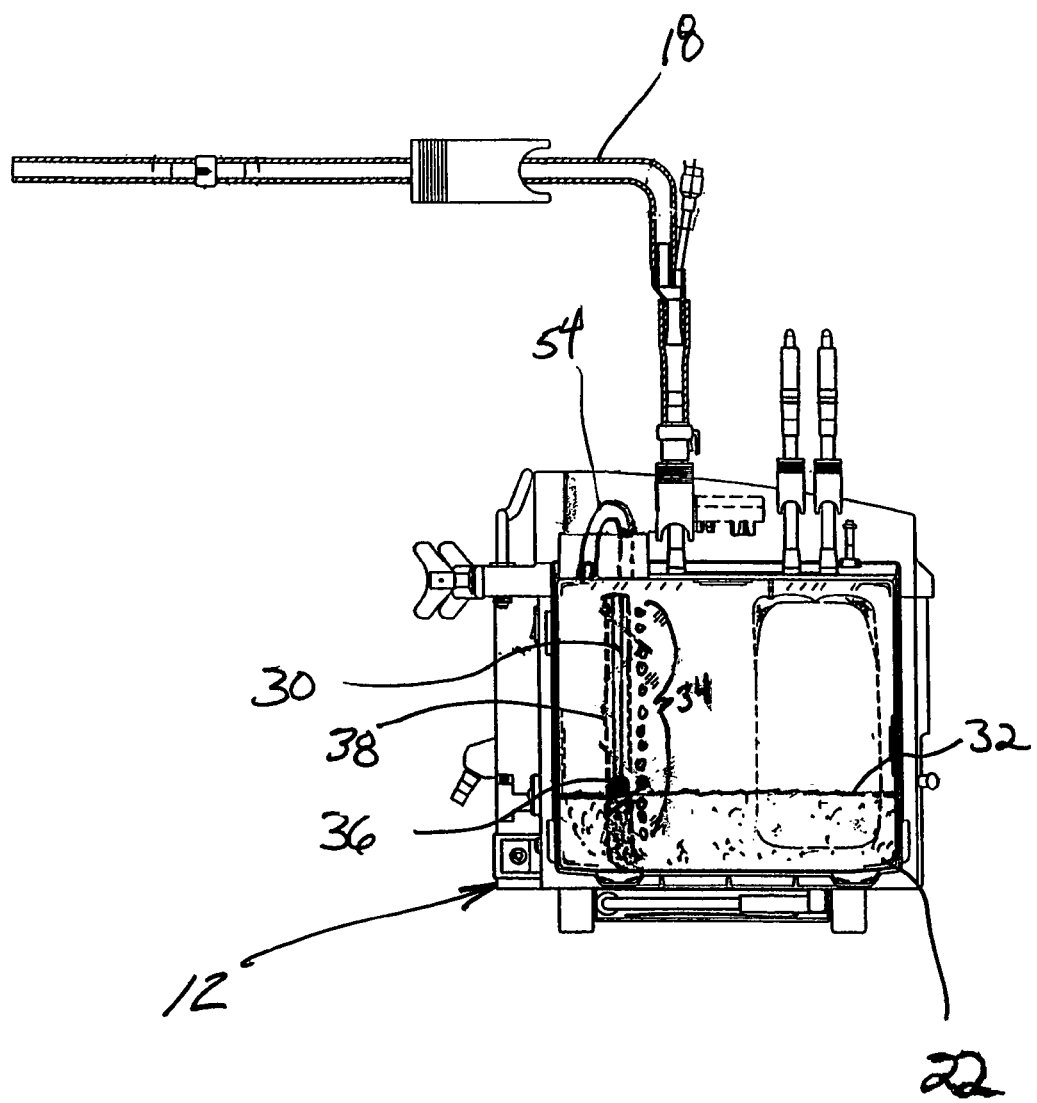
FIG. 3 is a side view of a fluid collection device.

FIG. 3 shows a side view of the postoperative fluid collection device 12. The fluid collection device 12 should have a liquid collection sensor for providing information to the controller regarding the volume of liquid collected during the drainage procedure. The sensor may be of a type that operates by optically determining the liquid level in the collection vessel. The sensor may include an optical observing means connected to the controller and an optical indicating means that is viewable by the optical observing means.

Figure 4:
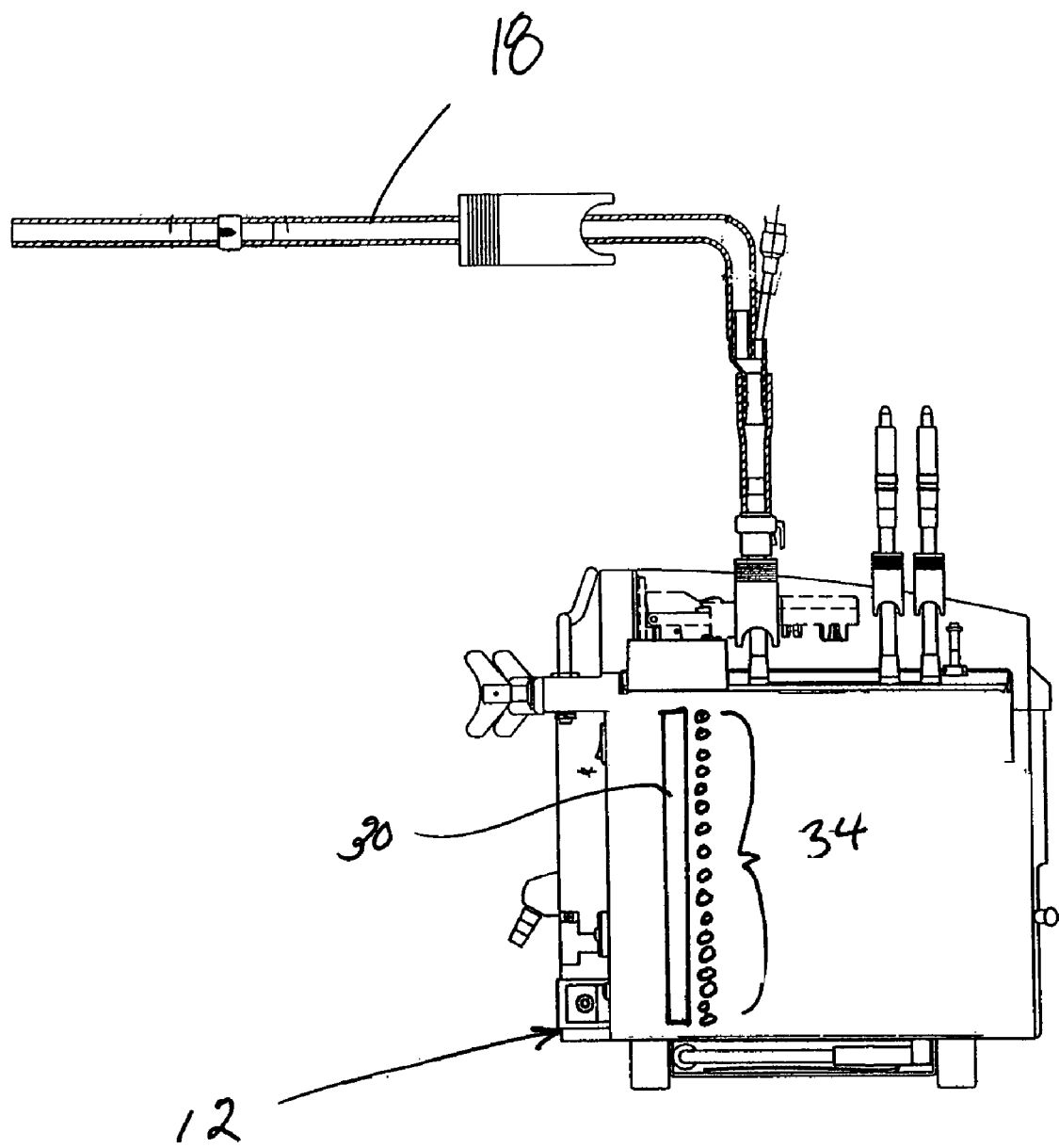
FIG. 4 is a side view of a fluid collection device with a fluid collection reservoir removed to show components of the liquid volume sensor.

Referring to FIGS. 3 and 4, the optical observing means of the liquid collection sensor comprises camera (not shown) mounted inside the fluid collection device housing. The camera observes liquid level 32 of liquid contained in the collection vessel 22. A slot 30 through the housing of the fluid collection device 12 provides a viewing port through which the camera can visually observe the surface level 32 of liquid collected in the collection vessel 20. When the collection vessel 22 is mounted to the side of the fluid collection device 12, the slot 30 aligns with a vertical column 38 that is housed in the vessel 20 and in fluid communication with its interior. A floating ball 36 is provided in the column that floats on the surface of the liquid surface level 32 while remaining constrained in the area of the vertical column. The ball enhances the visibility of liquid surface level 32 for the camera thereby providing the optical observing means component of the liquid collection sensor. Though the ball helps the camera distinguish where the liquid level begins, the camera views the entire column and detects area in the column not occupied by liquid as explained below.

To further assist the camera in accurately determining the liquid level 32 in the vessel 22, an array of lights 34 may be provided to illuminate the column 38 in the vessel. The camera can only view the bright reflections of the lights and does not observe opaque areas without reflection of the lights. Preferably the vertical column 38 is formed with a back surface of a bright, reflective color, such as white. Accordingly, when there is no liquid yet collected in the vessel 22 (and vertical column 38), the camera can view the entire column because the entire area is free from liquid and is reflective. The camera and controller interpret this condition as an empty vessel 22. As the liquid level 32 rises in the column, the camera detects only areas that are not occupied by liquid due to the reflection created in the column of the vessel by the array of lights 34. Liquid obscures the light's reflection on the surfaces of the collection vessel and therefore the camera does not sense that area of the column occupied by liquid. Because the total volume of the vessel is known and the amount of area in the vessel not occupied by liquid is detectable by the camera, the volume of liquid collected is calculated on an ongoing basis by the controller by subtracting the volume of the vessel not occupied by liquid from the known total volume of the vessel. A camera that has been found to operate successfully in monitoring the liquid level in the collection vessel in the manner described above is a Sony ILX 75IA Linear CCD Array.

With the presence of a suction valve 56 operated by the system controller, an additional monitoring and alarm feature can be provided with the system. If a vacuum leak along the suction pathway occurs, the pressure sensor 58 will detect that suction levels are repeatedly being reduced and will indicate to the controller that suction valve 56 should be opened to the vacuum reservoir to replenish the vacuum level in the suction pathway. The controller can be programmed to identify such a trend, indicative of a vacuum leak, by monitoring the times that the suction valve 56 opens and closes or by monitoring the information from the pressure sensor 58. If the suction valve opens and closes excessively (exceeding a predetermined a number programmed into the controller) an alert can be activated by the controller to notify the care provider that a vacuum leak may have occurred. The alert may comprise a visual notification on the visual display 26 and/or an audible alarm.

Vacuum leaks can occur at the interface between the drain catheter and access point to the internal areas of the patient. Also, a vacuum leak may occur at other points along the suction pathway, such as connection points of the device hardware or through a damaged component of the device hardware. The fluid drainage procedure will not be effective if adequate levels of suction cannot be generated in the suction pathway. With the monitoring and alarm system of the present invention, early notification to the care provider of the potential vacuum leak will result in corrective action being taken much sooner than if the trend pointing to such a problem were left to be noticed by the care provider on their periodic rounds.

Figure 5:
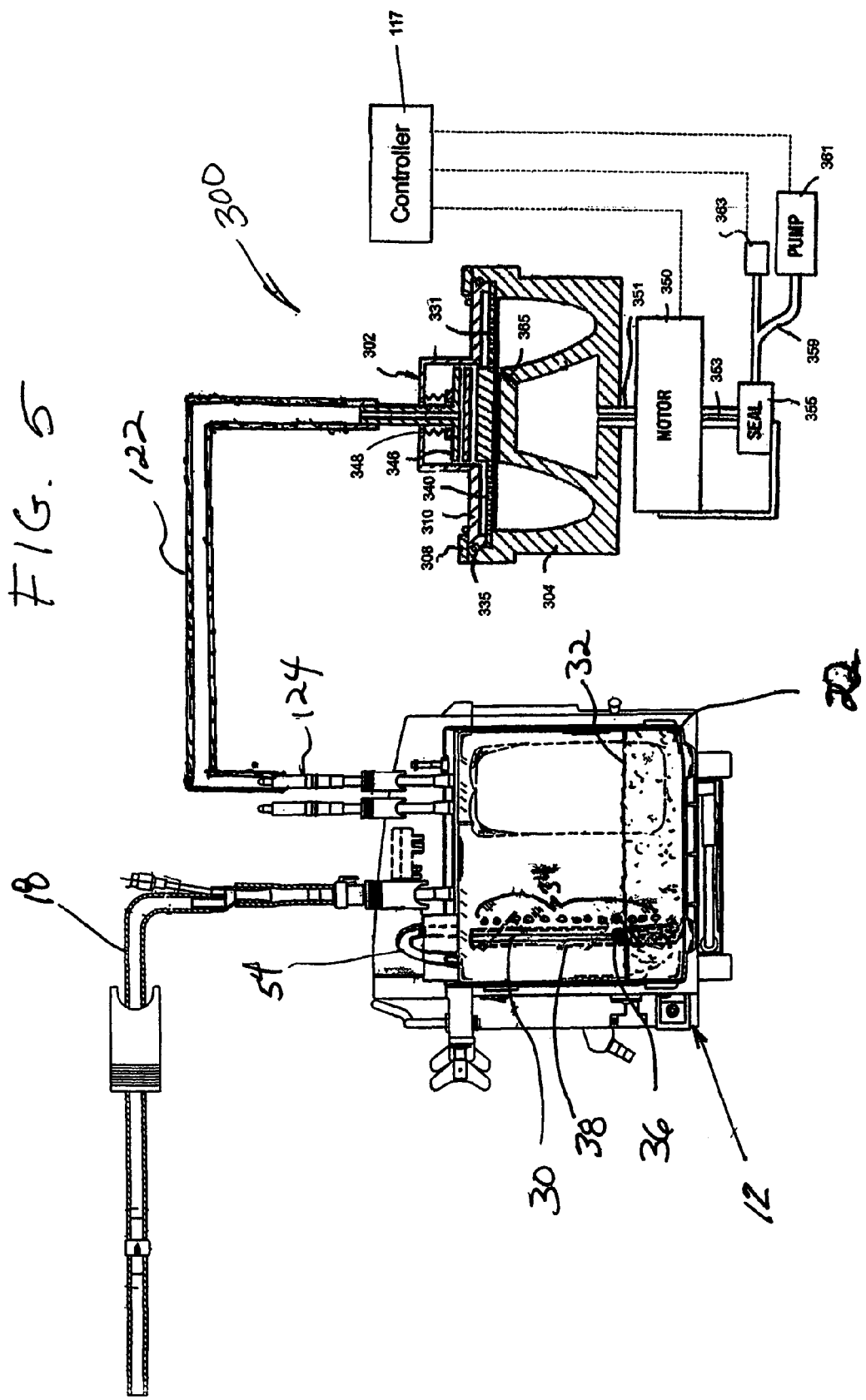
FIG. 5 is a diagrammatic illustration of a fluid collection vessel in communication with an autotransfusion device shown in cross section.

FIG. 5 shows components of the suction pathway and how they may be connected in combination with an autotransfusion device 300 capable of re-processing the blood that is collected and returning it to the patient for use. Though the autotransfusion device components may be housed together in the fluid collection device 12, they are shown separately in FIG. 5 in order to facilitate explanation of the several components and to show connection of the rotor with the suction pathway of the surgical wound drain. The autotransfusion device 300 may be configured as an Orthopat® manufactured by Haemonetics Corporation of Braintree, Mass. Primary features of the Orthopat® autotransfusion device are described in U.S. Pat. No. 5,733,253, the entirety of which is incorporated by reference herein.

The variable-volume rotor 302 illustrated is of a type described in U.S. Pat. No. 5,733,253 at FIGS. 1-4, although other rotors shown and described in this patent may be used as well, such as the rotors shown in FIG. 7, 8A, or 41 and 42 of that patent. The variable-volume rotor 302 has an elastic diaphragm 331 and a rigid member 310, which together define a chamber of varying volume, as described in U.S. Pat. No. 5,733,253. The rotor is in fluid communication with drain tube 18 and collection vessel 22 via rotor tube 122 that is connected to vessel fitting 124, which opens to the interior of the collection vessel. Fluid communication in and out of the rotor is provided by a collector assembly 346 which is attached to tube 122 and is connected to the rigid member 310 via a rotary seal 348. The tubing 122 and the collector assembly 346 are held stationary while the rest of the variable-volume rotor 302 rotates (i.e., the rigid wall 310 and the diaphragm 331). To protect the elastic diaphragm 331 while spinning from the stationary collector assembly 346, a perforate interior wall 340 is attached below the rigid wall 310. The perforate interior wall 340 includes holes that allow fluid communication between the areas of the chamber above and below the perforate interior wall 340.

In use, the variable volume rotor 302 is held onto and spun by a centrifuge chuck 304. The chuck 304 holds the rotor 302; the chuck 304 has a clamp 308 that holds the rotor 302 securely in place in the chuck 304, and an O-ring 335 that forms an air-tight seal. A drive motor 350 is connected to the chuck 304 by means of a shaft 351. In order to apply a vacuum or pressure to the rotor 302 to pump fluid in and out of the rotor, respectively, the shaft 351 has an axial hole through its center 353 and is connected to a rotary pneumatic seal 355, which in turn is connected by tubing 359 to a compressor/vacuum pump 361 and to a controllable exhaust valve 363. Holes 365 in the interior of the chuck 304 allow air to flow to and from the compressor/vacuum pump 361. These spinning and pumping mechanisms are controlled by a controller 117.

To draw blood from the wound, controller 117 controls the compressor/vacuum pump 361 to provide a vacuum through the chuck to the exterior side of the diaphragm 331. Because the diaphragm 331 is pulled downward by the vacuum in the chuck 304, an area of low pressure is created in the chamber, causing suction to be applied at the drain catheter 102. Consequently, fluid is drawn into the rotor 302 through the rotor tube 122. As more and more fluid enters the rotor 302, the diaphragm 331 changes shape to accommodate it. In this manner, blood and/or other fluid is drawn from the wound-drain site through the drain catheter, drain tube 18, collection vessel 22, associated tubing 122 and into the rotor 302.

The autotransfusion device controller 117 may be a separate controller from the controller 24 dedicated to the monitoring and alarm system or one controller may be used to perform both operations. If separate controllers are used they should be connected and configured to exchange information between them. Because the controller 24 keeps track of the total amount of liquid withdrawn from the patient based on the quantity of liquid in the collection vessel 22, it must integrate information regarding the amount of liquid that is withdrawn from the amount in the vessel to be processed by the autotransfusion device. To accurately monitor wound healing based on the quantity of blood and other fluids withdrawn from the surgical site, the total quantity of liquid collected must be known with accuracy. Therefore, liquid collected into the vessel 22 then later aspirated into the autotransfusion device 300 must be tracked and considered in the total amount of liquid collected. Because the total maximum volume of the autotransfusion device is known, the controller 24 need only receive information of when the aspiration is being initiated into the autotransfusion device. The amount of liquid that is removed from the collection vessel will be known. Controller 24 tracks of the amount of blood being processed and continues to add that amount to the amount actually observed in the vessel 22. Without this correction of the amounts actually observed in the vessel 22, the controller 24 would indicate only the amount of liquid observed in the vessel, which would be less than the actual total amount collected from the patient.

Figure 6:
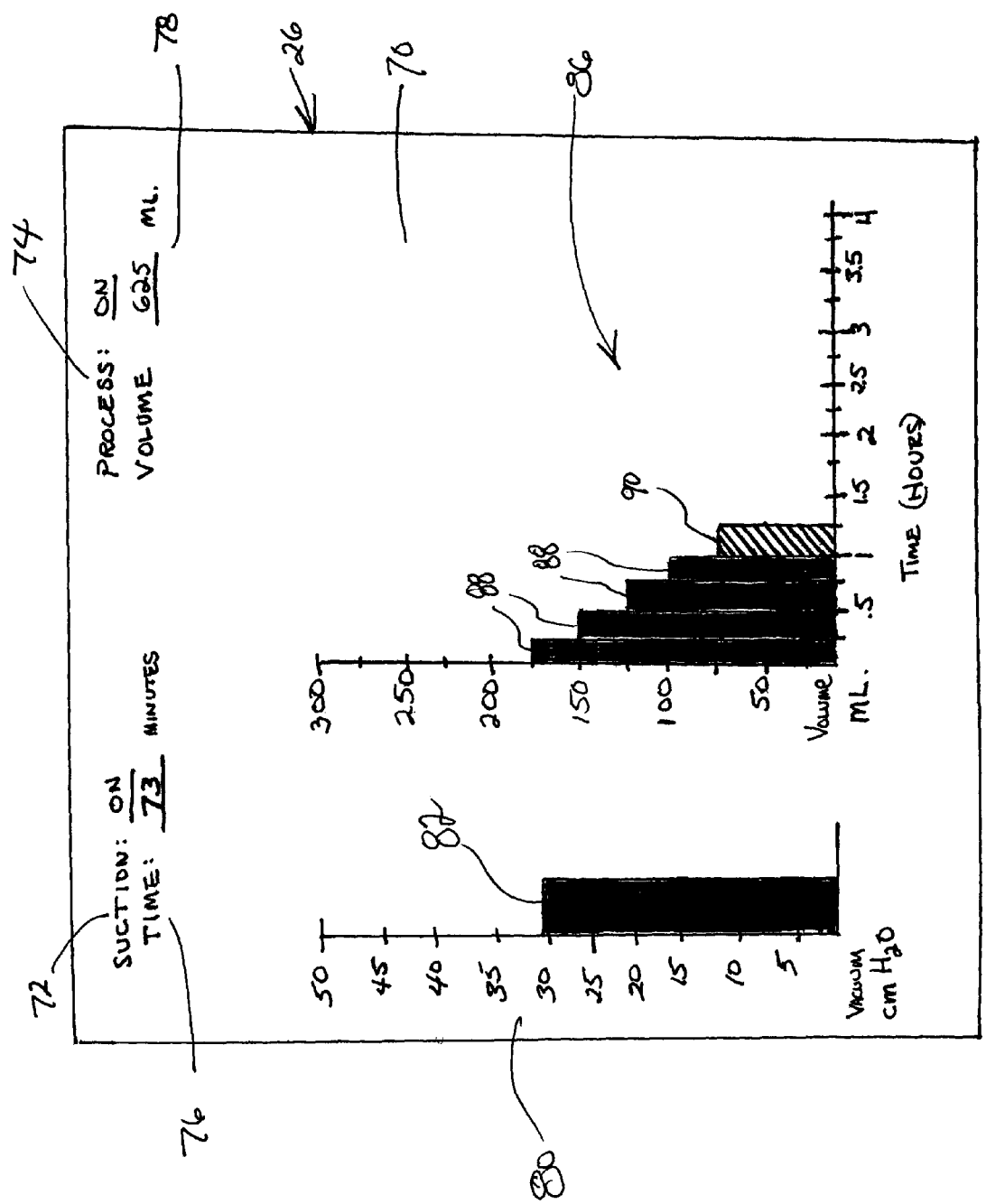
FIG. 6 is a representation of a visual display screen of the fluid monitoring and alert system in a normal postoperative surgical site drainage conditions.
Figure 7:
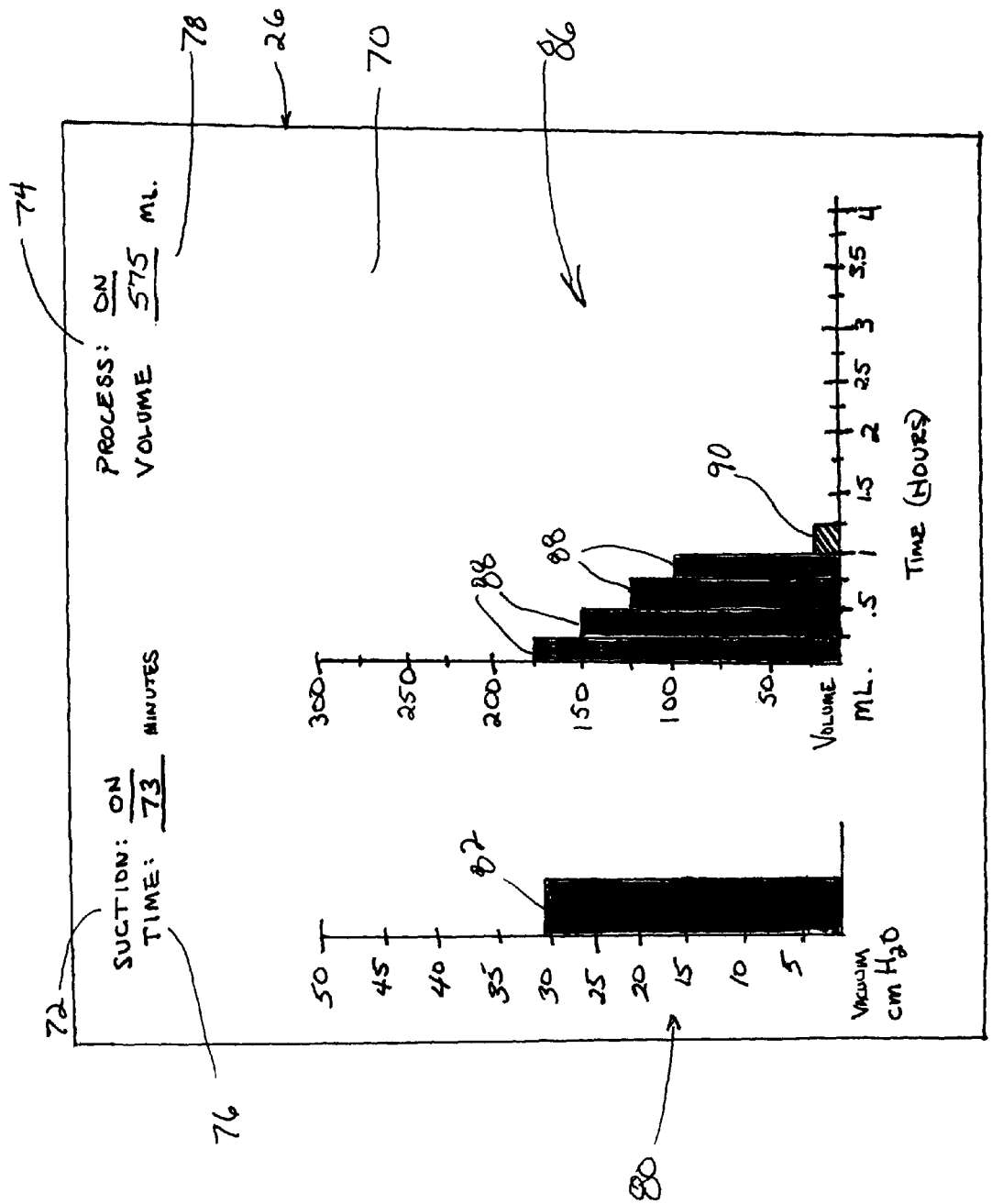
FIG. 7 is a representation of a visual display screen of the fluid monitoring and alert system under a postoperative condition of a blocked suction pathway.
Figure 8:
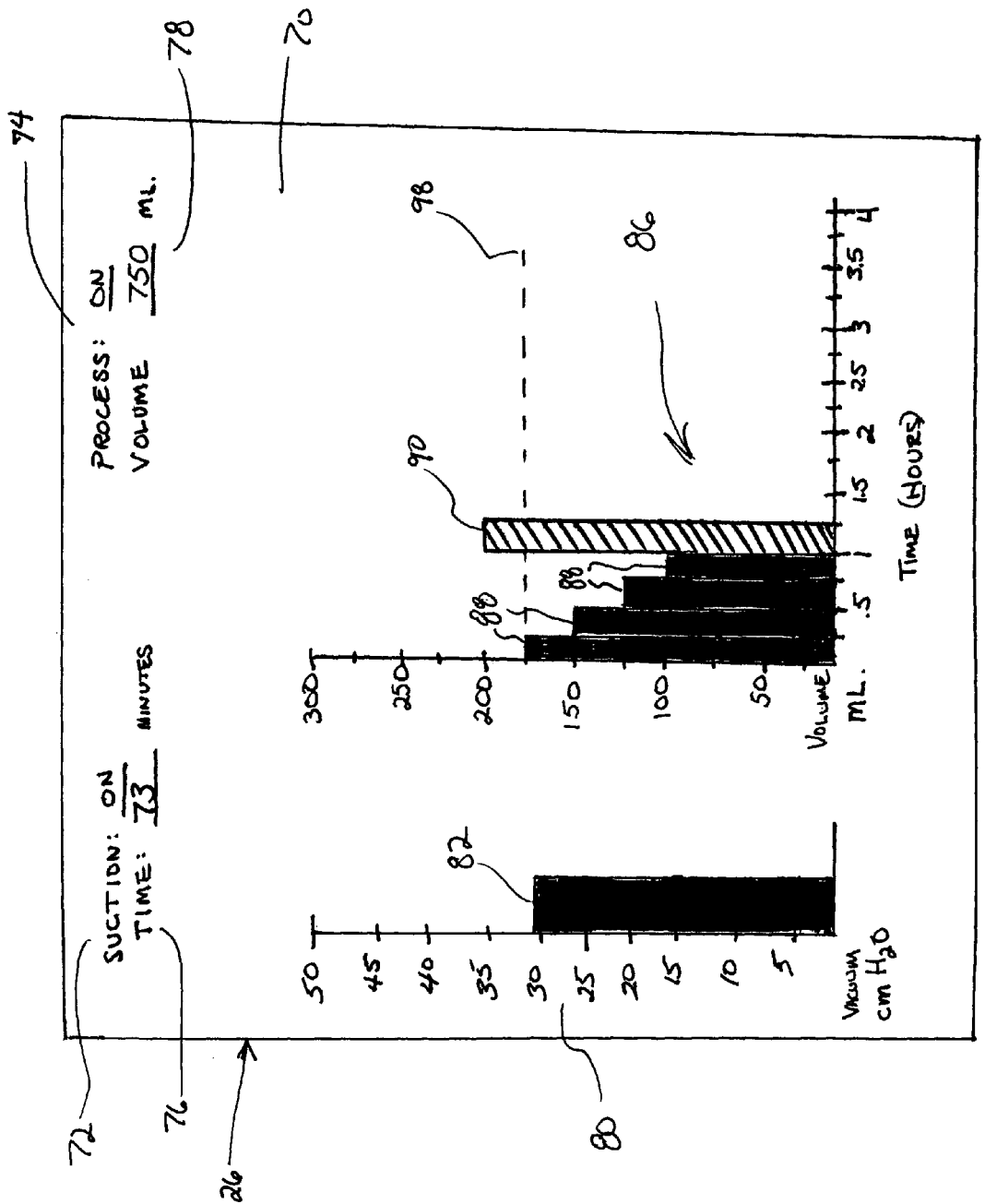
FIG. 8 is a representation of a visual display screen of the fluid monitoring and alert system under the postoperative condition of excessive bleeding at the surgical site.

FIGS. 6-8 are depictions of the visual display 26 under different performance conditions and being configured to inform the care provider of the status of the surgical wound drainage procedure. As shown in each of the FIGS. 6-8, one or more are graphical depictions as well as one or more alphanumeric data points may be shown. The visual display 26 may comprise a video screen 70. At the top of the screen may be displayed a suction indicator 72 that will alert the care provider that suction is either on or off. A drainage process indicator 74 that indicates whether the process is on, off or on standby may also be provided. A total time indicator 76 indicates the total amount of time that the procedure has run. A total volume indicator 78 also may be provided displaying a numerical total volume amount for liquid collected. Volume amounts may be shown in milliliters.

The display 26 may also present a graphical representation of the amount of suction being applied. A vacuum level graph 80 may be provided with units of vacuum measured in centimeters of $H_2O$ represented along the Y-axis with an active solid bar 82 extending vertically along the Y-axis to represent the level of vacuum present in the suction pathway. The vacuum reading in the graphical display is an instantaneous reading with the bar graph information being provided by the pressure sensor 58. The vacuum graph provides an indication to the care provider of the vacuum level at any given time and may be provided with upper and lower set points that trigger an alarm if the suction level migrates outside of the preferred operating parameters while the drainage process is on.

Another graphical representation may be provided for the user that indicates the amount of liquid collected over time. The liquid volume graph 86 may be configured to show the quantity of liquid collected for a finite time interval during the drainage process. The graph may show the amount of liquid collected for each past time period as well as the amount of liquid so far collected during the current time period. The graph 86 may be configured to show volume of liquid along the Y-axis in an appropriate unit size such as milliliters (ml). The X-axis may indicate time intervals, shown in hours with demarcations shown in 15 minute intervals. Accordingly, the bar graph can be displayed with each bar representing the amount of fluid collected during 15 minute periods of time.

The liquid volume graph 86 may show historical bars 88, representing the total amount of liquid collected during each past time interval. A distinct current bar 90 represents the amount of liquid collected so far during the current time interval. The current bar 90 is preferably visually distinguishable from historical bars 88, such as bar by being shown in a different color. In the example shown in the figures, the current bar 90 is a lighter shade, such as grey as compared to darker shading (such as black) for historical bars 88. The current bar 90 remains a distinguishable color until the 15 minute time interval has been completed at which point the total amount of liquid collected during that interval is known, the bar freezes at that volume level and changes to the dark color of the historical bars 88. At that point, a new current bar 90 will appear in the next time interval. Volume amount will increase as the amount actually collected increases because the liquid volume amount is continuously monitored. It is noted that the units and time intervals discussed above in connection with the graphical representations on the visual display 26 are intended to be illustrative only and other units and increments can be used without departing from the spirit of the invention.

The display of historical bars 88 in the volume graph 86 in conjunction with the current collection activity represented by current bar 90 facilitates the recognition and interpretation of trends occurring in the drainage procedure. Such trends may be indicative of the progress of the patient's recovery or of problems occurring in the drainage process. The volume graph 86 shown in FIG. 6 is indicative of a normal patient recovery after surgery. Each of the historical bars 88 indicate progressive reductions in volume of fluid collected for each time interval. Gradual and steady reduction in flow from the postoperative surgical site indicates normal wound healing. The current bar 90 shown in FIG. 6 represents a snapshot taken of the collection amount at a point in time that is substantially through the current time interval (snapshot taken at 13 minutes into the 15 minute current time interval).

The point in time the visual display is being observed is indicated by total time indicator 76 showing "73 minutes" total time elapsed. As shown in FIG. 6, the volume of liquid collected during the almost completed current time interval 90 is approximately 75 milliliters and represents a continuation of the gradual downward trend in the quantities of liquid collected. The normal progression of recovery indicated by the volume graph 86 in FIG. 6 will not trigger an alarm for the care provider and the process will continue uninterrupted.

FIG. 7 shows a visual display 26 configured identically to that shown in FIG. 6 with a volume graph 86 showing a trend that indicates a blockage in the suction pathway. In FIG. 7, current bar 90, again shown at 13 minutes into a 15 minute interval, shows a very small volume of liquid collected of only approximately 25 milliliters. The small amount of liquid collected represents a sudden and drastic reduction in the collected amount as compared to the closest historical bar 88 which indicated a collection level of approximately 100 milliliters. This sudden reduction of the amount of liquid collected represents a notable departure from the amounts indicated by the historical bars 88. A care provider observing the collection scenario shown in FIG. 7 should recognize that this trend may indicate a blockage in the suction pathway, such as in the drain tube.

The controller is programmed to compare current collection information with historical information and identify trends as would a care provider observing the data. Therefore, in comparing the flow information obtained during the current time interval with one or more of the historical time intervals, the controller can identify the discrepancy in the collection amounts based on comparison with preprogrammed acceptable values. When large variations from the programmed acceptable values are noted, an alarm is activated to alert the care provider about the trend so that investigation and any necessary corrective action can be undertaken.

In comparing collection information, the controller may use instantaneous data and need not wait for the completion of a time interval in order to make the necessary calculations to identify a trend indicative of a condition that may be harmful to the patient. The number of historical data points with which current data is compared may be varied in the programming of the controller to achieve the desired sensitivity of the monitoring and alarm system.

FIG. 8 again shows the visual display 26 with a liquid volume graph 86 indicating another type of suspect collection trend. In particular, current bar 90 indicates a sudden and dramatic increase in the quantity of liquid collected as compared to the historical bars 88. In a postoperative environment, a sudden increase in the amount of liquid collected, mostly blood, after a downward trend in the amount of liquid collected in each of the previous historical time periods is indicative of a new bleeding problem at the surgical site. The sudden increase in the amount of blood collected suggests that the surgical site may have opened permitting profuse bleeding in the area, which would require attention by the care provider to prevent patient harm.

In the example of FIG. 8, current bar 90 indicates that 200 milliliters of liquid has been collected as of 13 minutes into the current 15 minute time interval. The 200 milliliter amount is double the amount of liquid collected for the previous time interval and even exceeds the amount collected during the first time interval immediately following the surgical procedure. The controller is programmed to activate an alarm to notify the care provider of the sudden increase in liquid collected. The controller can also be programmed to have an upper acceptable limit for liquid collected such that an alarm will sound if that amount is exceeded during any time interval. The upper level is indicated by dashed line 98 corresponding to 175 milliliters of liquid. With an active upper limit alarm in place, a surgical site that begins bleeding profusely can be detected immediately without awaiting calculation of the trending algorithms by the controller.

It should be understood, however, that the foregoing description of the invention is intended merely to be illustrative thereof and that other modifications, embodiments and equivalents may be apparent to those skilled in the art without departing from its spirit.

Having thus described the invention what we desire to claim and secure by Letters Patent is:

1. A postoperative fluid monitoring and alert system comprising:
    a fluid collection device having a vacuum reservoir configured to be placed in communication with a suction pathway that is at least partially defined by a surgical drain tube;
    at least one liquid collection sensor configured to obtain data from the suction pathway;
    a controller connected to the sensor and configured to receive current procedure data from the sensor, save the data to create historical procedure data, compare the current procedure data to the historical procedure data and activate an alarm when predefined trends in the data are detected.

2. A postoperative fluid management system as defined in claim 1 wherein:
    the controller monitors communication between the vacuum reservoir and suction pathway and is configured to activate an alarm when communication is opened between the reservoir and pathway excessively.

3. A postoperative fluid management system as defined in claim 2 wherein: the vacuum reservoir is selectively opened to the suction pathway by a valve connected to the controller and the frequency of valve opening is monitored by the controller.

4. A postoperative fluid management system as defined in claim 3 wherein the controller activates opening of the valve based on pressure data received from a pressure sensor in fluid communication with the suction pathway.

5. A postoperative fluid management system as defined in claim 4 wherein: the vacuum reservoir is a closed tank connected to a compressor configured to be selectively operated to generate vacuum in the tank.

6. A postoperative fluid management system as defined in claim 4 wherein the vacuum reservoir is joined to a facility-wide source of suction.

7. A postoperative fluid management system as defined in claim 1 further comprising a visual display connected to the controller and being configured to display information regarding liquid collection volume over predetermined time intervals during a fluid drainage procedure.

8. A postoperative fluid management system as defined in claim 1 wherein the alarm is an audible alarm.

9. A postoperative fluid management system as defined in claim 7 wherein the alarm comprises a visual indication on the visual display.

10. A postoperative fluid management system as defined in claim 1 wherein the fluid collection device comprises an autotransfusion device.

11. A postoperative fluid management system as defined in claim 10 wherein the autotransfusion device is a peri-operative system and the controller is provided with intra-operative and postoperative modes of operation.

12. A postoperative fluid management system as defined in claim 7 wherein historical procedure data and current procedure data is displayed on the visual display graphically indicating the volume of liquid collected in fifteen minute time intervals.

13. A postoperative fluid management system as defined in claim 12 wherein historical procedural data from a plurality of previous time intervals are displayed on the visual display along with the current procedure data.

14. A postoperative fluid monitoring and alert system comprising:
- a fluid collection device having a vacuum reservoir configured to be placed in communication with a suction pathway that is at least partially defined by a surgical drain tube;
- at least one liquid collection sensor configured to obtain data from the suction pathway;
- a controller connected to the sensor and having instructions to receive current procedure data from the sensor, save the data to create historical procedure data, compare the current procedure data to the historical procedure data and activate an alarm when predefined trends in the data are detected.

* * * * *